United States Patent [19]

Brown et al.

[11] Patent Number: 4,904,950
[45] Date of Patent: Feb. 27, 1990

[54] TELEMETRY DIGITAL SUBCARRIER DEMODULATOR

[75] Inventors: Jay E. Brown, La Canada; Gary M. Zednick, Valencia; Bibiano P. Costello, North Hollywood, all of Calif.

[73] Assignee: Medical Data Electronics, Inc., Arleta, Calif.

[21] Appl. No.: 267,024

[22] Filed: Nov. 4, 1988

[51] Int. Cl.$^4$ ................................................ H03D 3/00
[52] U.S. Cl. ..................................... 329/341; 455/214; 340/870.18; 128/903
[58] Field of Search ...................... 329/110, 122, 126; 375/80, 82, 94, 96, 99, 100; 455/214; 340/870.18, 870.4; 128/903

[56] References Cited

U.S. PATENT DOCUMENTS

| | | | |
|---|---|---|---|
| 3,986,498 | 10/1976 | Lewis | 340/870.18 X |
| 4,757,520 | 7/1988 | Fujimoto | 329/126 X |
| 4,777,450 | 10/1988 | Rogers | 329/126 X |

Primary Examiner—Siegfried H. Grimm
Attorney, Agent, or Firm—Lyon & Lyon

[57] ABSTRACT

A telemetry receiver for demodulating subcarrier frequencies is disclosed. The flexibility of the receiver permits it to decode signals from a wide variety of transmitters. In the preferred embodiment, a biomedical digital telemetry subcarrier demodulator employs microprocessor control of a variable bandpass filter and cycle counter. The bandpass of the filter is set by the microprocessor to pass frequencies at and around the center frequency of the desired subcarrier frequency. The counter is preset for the desired number of cycles. In operation, the desired subcarrier frequency is passed by the filter, through a signal shaper, and to the counter. Upon receiving the first cycle, the counter activates a timer, which measure the period of the predetermined number of cycles. The desired signal is the percentage deviation of the subcarrier period from the average subcarrier period. The signal to noise ratio in a digital circuit may be improved by modulating the frequency of the clock supplied to the digital circuitry coupled with passing the signal through a bandpass filter whose passband is sufficiently narrow that interference signals caused by the clock will be within the passband a portion of the time and outside the passband a portion of the time.

11 Claims, 3 Drawing Sheets

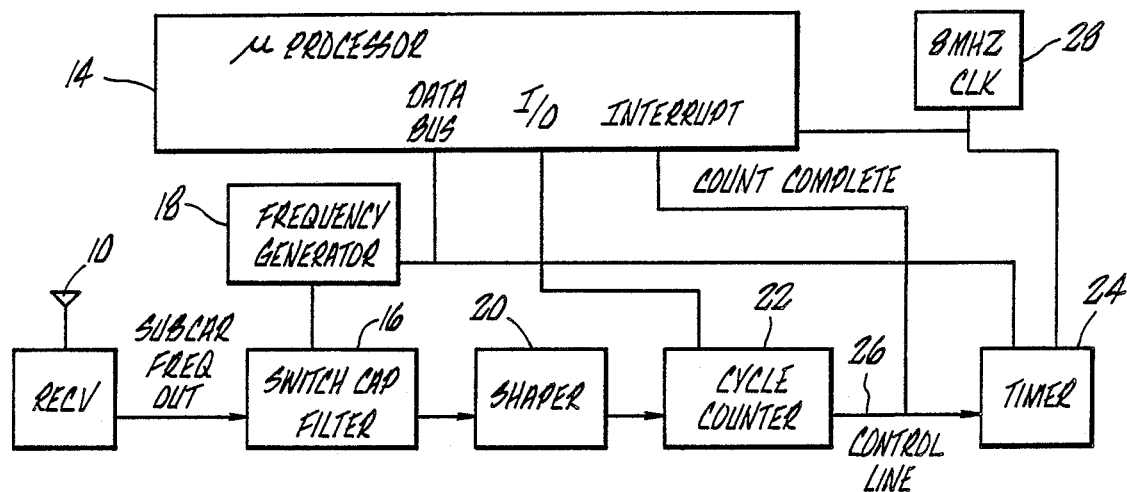
FIG._1_
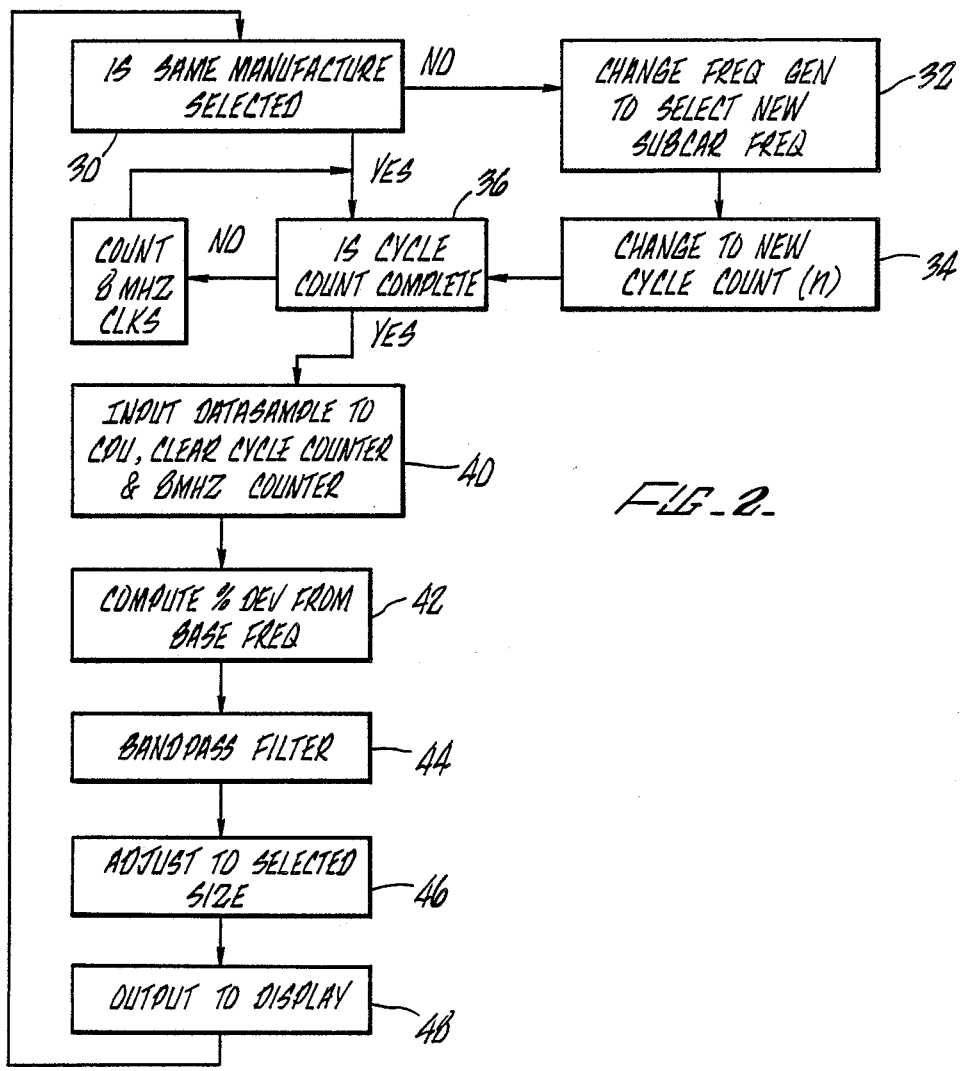
FIG._2_

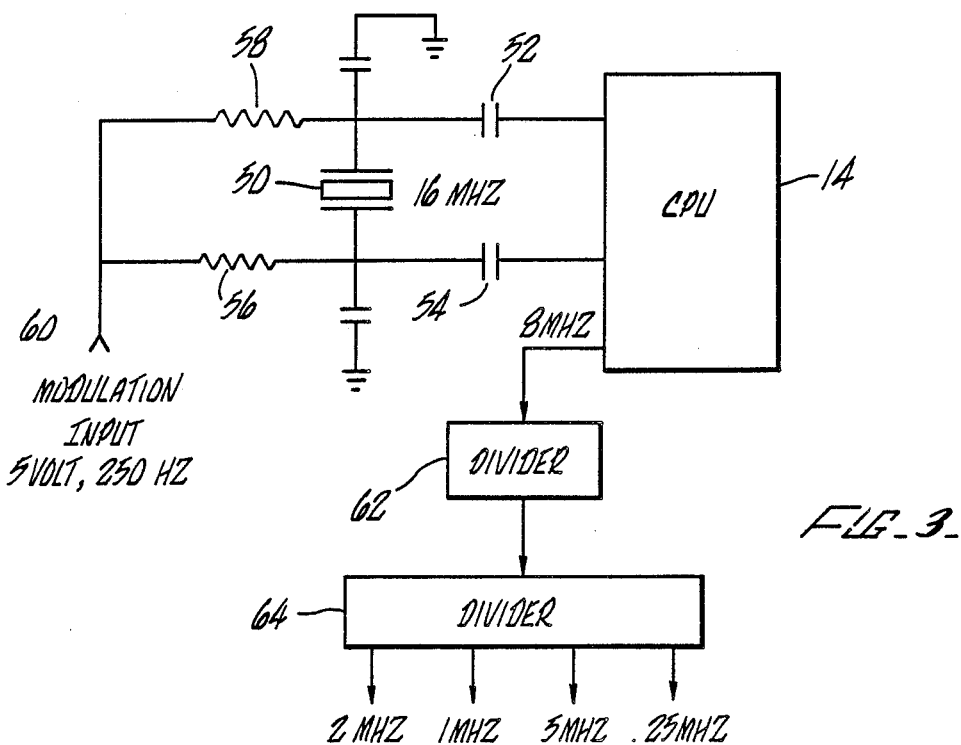
FIG_3.
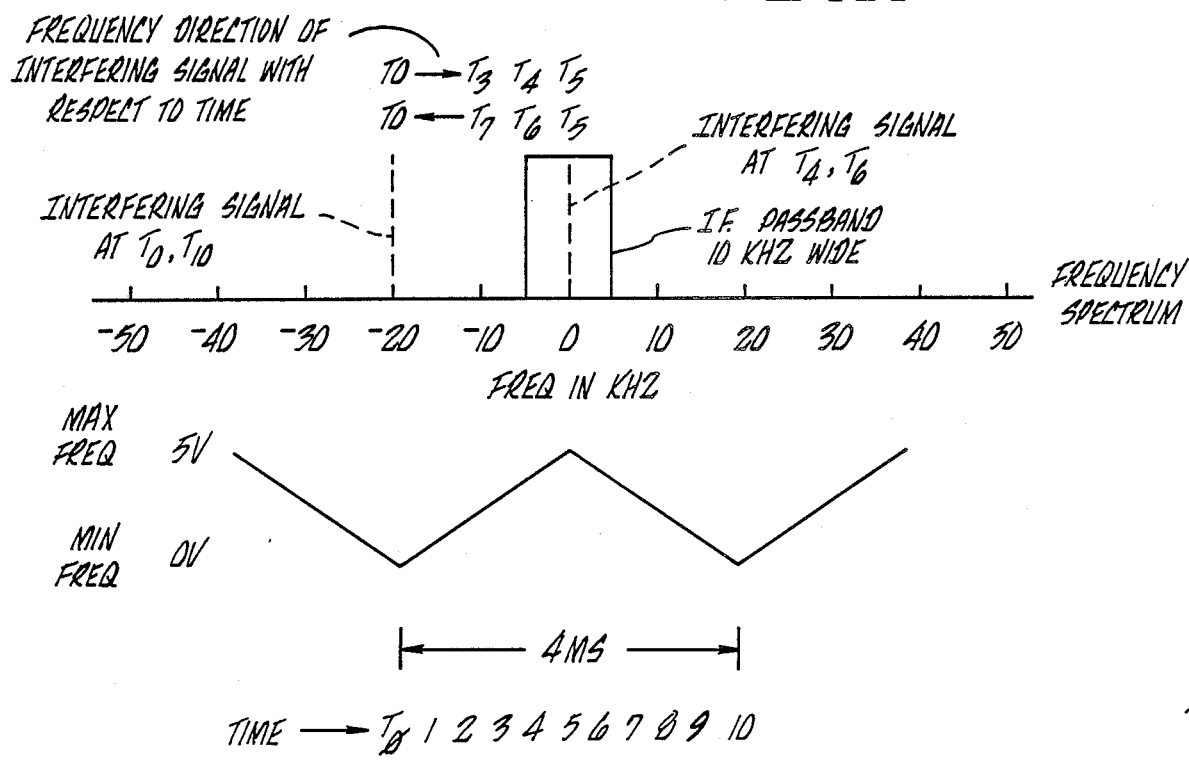
FIG_4.

TELEMETRY DIGITAL SUBCARRIER DEMODULATOR

FIELD OF THE INVENTION

This invention relates to a telemetry receiver for demodulating subcarrier frequencies, and in particular, to a biomedical telemetry digital subcarrier demodulator.

BACKGROUND

The process of telemetry involves the transmission of data from a source to a receiver typically by radio frequency electromagnetic means. Telemetry has been successfully used in biomedical applications to permit the remote monitoring of patients. An example of a useful signal to be remotely monitored is the electrocardiogram ("ECG"). A transmitter attached to a patient sends an ECG signal to a remote receiver where it is decoded and monitored. Such biomedical telemetry permits the patient greater mobility than if he were attached to a stationary monitor, thus enhancing the therapeutic benefits from patient mobility.

Transmitters for biomedical telemetry typically use a double frequency modulation ("FM") scheme for encoding and transmitting the signal. The signal is encoded as a frequency modulation of a subcarrier, which is in turn modulated on a carrier frequency. In the case of an ECG signal, the subcarrier is typically deviated at $+-20$ Hz to $+-300$ Hz, the amount of frequency deviation being proportional to the ECG signal at the input to the transmitter. The typical subcarrier frequency is from 1 to 10 kHz, and the typical carrier frequency is in the range of either 174 to 216 Mhz or 450 to 470 Mhz. Ordinarily, the transmitter is designed by the manufacturer to operate at a set subcarrier and carrier frequency.

In typical telemetry applications, a receiver is employed which demodulates the carrier first. The subcarrier detection is then done with an analog circuit tuned to a particular transmitter characteristic. Such analog circuits are not designed to be changed by the user to permit their use with subcarrier frequencies for other manufacturers transmitters. Accordingly, such dedicated analog receiver circuits are not usable for decoding the subcarrier frequencies of a variety of manufacturers. Thus, if numerous transmitters with different subcarrier frequencies are being used, more than one receiver must be used.

One example of such a prior art biomedical telemetry demodulator is the Medical Data Electronic, Inc. ESCORT MODEL 1000 PORTABLE TELEMETRY STATION. Analog subcarrier detection circuitry is used which is set by the manufacturer to detect a fixed number of subcarrier frequencies used by one transmitter manufacturer.

Considering now the use of analog decode circuitry versus digital decode circuitry, a known disadvantage of using a digital circuit for purposes of radio frequency reception and demodulation is that the clock for the microprocessor can interfere with the desired signal. This has the undesired effect of reducing the signal to noise ratio for the desired signal.

SUMMARY OF THE INVENTION

This invention discloses a method and apparatus for decoding telemetry signals from a variety of transmitters using various carrier and subcarrier frequencies. More particularly, this invention relates to a programmable receiver for biomedical telemetry capable of decoding signals from any number of transmitters operating at different carrier and subcarrier frequencies.

A programmable microprocessor controlled circuit receives the subcarrier frequency from a conventional receiver. The subcarrier is passed through a switched capacitor filter to provide a band pass filter, the center frequency of the switched capacitor filter being set by the microprocessor to correspond to the subcarrier center frequency of the transmitter. The sampled average period of the subcarrier is determined by measuring the elapsed time for a predetermined number of cycles of the subcarrier. The desired signal is determined by measuring the difference between the sampled time period for the subcarrier and the 3 second averaged period for the subcarrier. The signal may then be filtered, sized and displayed as desired.

The crystal clock for the microprocessor is frequency modulated or dithered (hereinafter "dithered") in order to reduce interference. The crystal may operate, for example, at 16 Mhz. Interference arises due to the harmonics of the crystal frequency or related clocks providing energy to the receiver. By dithering the crystal frequency, the amount of time that an interfering signal is included within the receiver pass band is reduced. A significant improvement in the signal to noise ratio may be achieved.

Accordingly a principal object of this invention is to provide a universal method and apparatus for decoding telemetry signals of different carrier and subcarrier frequencies.

It is a particularly object of this invention to provide a universal biomedical telemetry receiver capable of decoding the biomedical telemetry signals from a wide variety of transmitter manufacturers.

It is an object of this invention to provide a programmable microprocessor circuit capable of demodulating various subcarrier center frequencies and deviations thereof.

It is a further object of this invention to provide a telemetry receiver having an improved signal to noise ratio.

It is an object of this invention to provide a biomedical telemetry receiver employing a dither circuit to vary the clock frequencies used in the digital circuitry to reduce interference.

BRIEF DESCRIPTION OF THE DRAWINGS

FIG. 1 is a block diagram of the telemetry decode hardware.

FIG. 2 is a flowchart of the telemetry decode operation.

FIG. 3 is a schematic of the dither circuit.

FIG. 4 is a diagrammatic representation of the effect of the dither circuit.

DETAILED DESCRIPTION OF THE PREFERRED EMBODIMENT

FIG. 1 is a block diagram of the telemetry decoder hardware in the preferred embodiment. A conventional antenna 10 and receiver 12 are capable of receiving and demodulating the carrier signal. A microprocessor 14, for example a Hitachi 64180 microprocessor, provides control functions for the circuit. Conventional supporting circuitry for the microprocessor (not shown) is employed as known to those skilled in the art, and would include a crystal clock generator and memory. A switched capacitor filter 16 is located downstream of the receiver 12. The filter 16 is a bandpass filter, whose center frequency is determined in response to a frequency supplied to it by the frequency generator 18. The frequency generator 18 is in turn provided a signal under control of the microprocessor 14 which has been selected based upon the subcarrier frequency of the transmitter. The output of the switched capacitor filter 16 is passed to a shaper 20 which converts the generally sine wave output of filter 16 into a square wave output from the shaper 20. The output of shaper 20 is fed to cycle counter 22 which is capable of being set by the microprocessor 14 to count a predetermined number of cycles. The output of cycle counter 22 is passed to the timer 24 via control line 26. A crystal clock 28 provides clock signals to the timer 24 and microprocessor 14. More than one clock signal may be used, and the clock signals may be independently either dithered (as described in detail below), or not, as necessary for purposes of noise reduction.

The intended operation of the telemetry decode circuit can be understood with reference to the hardware description of FIG. 1 and the flowchart description of FIG. 2. Initially, the microprocessor 14 must be provided with an input as to the type of transmitter being used. This may be either input by the operator of the receiver or may be determined by the receiver, for example by a scanning of the possible subcarrier frequencies. Based upon the identity of the transmitter, the microprocessor 14 will retrieve from memory (not shown) information relating to the number of cycles of the subcarrier to be counted and will preload the cycle counter 22 with that information. At that point, the control line 26 to the timer 24 is at the "OFF" level. Further based on the selection of the transmitter, the microprocessor 14 will condition the frequency generator 18 to output the appropriate center frequency for the bandpass filter 16.

In operation, the telemetry signal will be received by the antenna 10, demodulated by the conventional receiver 12, and the modulated subcarrier frequency output to the subcarrier decoder. The switched capacitor filter 16 will then pass the subcarrier signal at and around the frequency determined by the frequency generator 18 to the shaper 20. The shaper will convert the generally sinusoidal output of the filter 16 into a square wave. When the first cycle is detected by the cycle counter 22, the control line 26 is set to the "ON" level. The timer 24 then begins measuring the elapsed time. Typically, the timer counts pulses of the clock 28. When the cycle counter 22 has counted the preset number of cycles, the control line 26 is again set to the "OFF" level. This causes the timer 24 to stop counting pulses from the clock 28, and will signal the microprocessor 14 through the interrupt port that the cycle count has been completed. The sample in the timer 24 is then input to the microprocessor 14 over a data bus. Another cycle count is immediately started.

The average period of one subcarrier cycle is then calculated from the total accumulated clock cycles from clock 28 and from knowing the number of cycles counted by the cycle counter 22. This average period is called the DATASAMPLE. The DATASAMPLE is held by the microprocessor 14 associated memory. The cycle counter 22 and timer 24 are then reset as shown in step 40 of FIG. 2.

The desired signal is then calculated by computing the percentage deviation of the subcarrier frequency from the base or average frequency of the subcarrier as shown in step 42. Specifically, since the desired signal is the deviation of the subcarrier frequency from the center frequency, the signal is given by the following equation, assuming a three second averaging period:

DATASAMPLE PERIOD—3 SECOND AVERAGE OF DATA SAMPLES

In the example of this detailed description, the ECG signal has now been recovered.

The desired signal is then applied to a digital bandpass filter as shown in step 44. For an ECG signal, the bandpass values would be approximately 0.5 Hz to 40 Hz. The filtered signal is then sized in accordance with a user selected size control as shown in step 46. The resultant signal is then output to a suitable display as shown in step 48.

When using the telemetry decode circuitry for another transmitter, it is necessary to determine whether the transmitter subcarrier frequency is the same as previously used. If it is not, the microprocessor 14 must be provided with information indicating what type of transmission unit is in use, as shown in step 32. As described previously, this will use a new maximum cycle count to be loaded into the cycle counter 22 and the appropriate signal applied to the frequency generator 18 so as to generate the appropriate bandpass center frequency as shown in step 34. At this point, if a cycle count is in progress further action will be delayed until the count is complete as shown in steps 36 and 38. Operation of the telemetry decode circuit then continues as described above.

The microprocessor will operate at a basic clock frequency, typically 16 Mhz. The output frequency of the microprocessor 14, typically 8 Mhz, will be further divided through dividers 62 and 64 into a variety of frequencies, as necessary. The harmonics of the basic clock frequency and divided frequencies will have enough energy at frequencies below 250 Mhz to cause interference in the medical telemetry band. For example, 0.25 Mhz clock has 168 harmonics which fall in the band from 174 Mhz to 216 Mhz.

FIG. 3 shows a simplified schematic diagram of a dither circuit. The quartz crystal clock 50 is connected to the microprocessor 14 via capacitors 52 and 54. A modulation input voltage 60 is impressed across the crystal 50 via parallel resistors 56 and 58. In the preferred embodiment, the modulation input signal 60 is a 5 volt ramp voltage at approximately 250 Hz.

By way of example, if the crystal 50 has a frequency of 16 Mhz, and if the dither frequency is $+-2$ kHz at approximately a 250 Hz rate, a 14 decibel improvement in signal to noise ratio is realized. In this example, a telemetry channel at 196 Mhz would be the 48 harmonic for a 4 Mhz clock signal. In this example, the 4 Mhz clock would be dithering at $+-500$ Hz and the 48 harmonic of the 4 Mhz clock is dithering at $+-24$ kHz.

Referring to FIG. 4, the frequency spectrum has its zero at the carrier frequency. The interfering signal frequency deviation is shown by the vertical line 72 and will sweep the frequency spectrum in time. At time T=0 the interfering clock signal 72 is outside the passband 70 of the receiver. At time T3 the interfering signal enters the lower side of the passband 70 until at time T5 it reaches the higher side. At that point the interfering signal 72 retraces and decreases in frequency. At time T7 the interfering signal 72 would leave the passband 70 as it proceeds back to its starting frequency. Thus, the dithering process moves the interfering clock signal 72 into and out of the passband 70 at a 250 Hz rate. In this example the interfering signal 72 is in the passband 70 for 0.8 milliseconds and out of the passband 3.2 milliseconds. In this way a 12 decibel,(20 log (3.2/0.8)), improvement in signal to noise ratio can be achieved.

Though the invention has been described with respect to its specific preferred embodiment thereof, many variations and modifications will become apparent to those skilled in the art. It is therefore the intention that the appendant claims be interpreted as broadly as possible in view of the prior art to include all such variations and modifications.

What is claimed is:

1. A biomedical telemetry signal decode circuit comprising:
   filter means for selecting a desired passband arranged to receive said signal,
   a cycle counter arranged to receive the output of said filter means,
   a timer to receive a signal output from the cycle counter and
   a microprocessor for control of the decode circuit.

2. The biomedical telemetry decode circuit of claim 1 wherein the filter means includes a frequency generator and switched capacitor filter.

3. The biomedical telemetry decode circuit of claim 1 which further comprises a shaper disposed between the filter and the cycle counter.

4. A variable decoder for use in telemetry comprising:
   a variable bandpass filter,
   a cycle counter coupled to the filter,
   a timer coupled to the cycle counter, and
   control circuitry to set the passband of the variable bandpass filter, to set the cycle counter and to receive the result from the timer.

5. A biomedical telemetry digital subcarrier demodulator comprising:
   a switched capacitor filter disposed to receive the subcarrier,
   a frequency generator for the switched capacitor filter,
   a shaper to convert the output of the filter to a square wave,
   a cycle counter disposed to receive an output from the shaper,
   a timer controlled by the cycle counter, and
   a microprocessor for control of the demodulator.

6. A method of demodulating a subcarrier signal comprising the steps of:
   filtering the subcarrier through a variable bandpass filter, counting a predetermined number of cycles of the filtered subcarrier signal,
   measuring the time for the predetermined number of cycles, generating an average period for the filtered subcarrier signal,
   determining the demodulated subcarrier signal by determining the percentage deviation of the period of the filtered subcarrier signal from the average period for the filtered subcarrier signal.

7. The method of demodulating a subcarrier signal of claim 6 wherein the filtered subcarrier signal is shaped prior to the counting step.

8. A method for reducing interference with a signal in a digital demodulator circuit comprising:
   modulating the frequency of the clock signals in the digital demodulator circuit,
   passing the signal through a bandpass filter whose passband is sufficiently narrow that interference signals caused by the clock signals will be within the passband a portion of the time and outside the passband a portion of the time.

9. A biomedical telemetry digital subcarrier demodulator comprising:
   a microprocessor,
   a clock operatively connected to the microprocessor,
   a dither circuit associated with the clock for causing the clock frequency to modulate,
   a variable bandpass filter to receive an unfiltered signal,
   a cycle counter to receive the output of the filter and
   a timer to receive output from the cycle counter.

10. The biomedical telemetry digital subcarrier demodulator of claim 9 wherein the variable bandpass filter includes a switched capacitor filter.

11. The biomedical telemetry digital subcarrier demodulator of claim 9 further including a signal shaper.

* * * * *